United States Patent
Yamamoto et al.

[11] Patent Number: 6,139,767
[45] Date of Patent: Oct. 31, 2000

[54] CARBOXYLATED POLYMERS, PROCESS FOR THE PRODUCTION OF THE SAME, AND GELS THEREOF

[75] Inventors: Hiroshi Yamamoto; Yoshiaki Hirano, both of Suita; Hisakazu Shindo, Himeji; Hirokazu Ito, Kobe, all of Japan

[73] Assignee: Nippon Shokubai Co., Ltd., Osaka, Japan

[21] Appl. No.: 08/983,481

[22] PCT Filed: May 16, 1997

[86] PCT No.: PCT/JP97/01669

§ 371 Date: Jan. 22, 1998

§ 102(e) Date: Jan. 22, 1998

[87] PCT Pub. No.: WO97/44369

PCT Pub. Date: Nov. 27, 1997

[30] Foreign Application Priority Data

| May 22, 1996 | [JP] | Japan | 8-127523 |
| May 22, 1996 | [JP] | Japan | 8-127525 |
| May 22, 1996 | [JP] | Japan | 8-127526 |
| May 22, 1996 | [JP] | Japan | 8-127527 |
| May 22, 1996 | [JP] | Japan | 8-127528 |

[51] Int. Cl.$^7$ .............. C02F 5/10; C08F 28/06; C08F 226/12; C08F 228/02

[52] U.S. Cl. .............. 252/180; 423/DIG. 14; 516/102; 516/108; 524/916; 525/919; 526/258; 526/260; 526/286; 526/288; 526/317.1

[58] Field of Search .............. 516/102, 108; 526/286, 288, 317.1, 260, 258; 524/916; 525/919; 521/37; 423/DIG. 14; 252/184, 180

[56] References Cited

U.S. PATENT DOCUMENTS

| 3,090,771 | 5/1963 | D'Alelio | 526/288 X |
| 3,265,673 | 8/1966 | Richards et al. | 526/288 X |
| 3,314,857 | 4/1967 | Fainer . | |
| 3,933,940 | 1/1976 | Anderson et al. | 526/286 X |
| 4,024,073 | 5/1977 | Shimizu et al. | 576/102 |
| 4,618,448 | 10/1986 | Cha et al. | 252/180 |
| 4,762,556 | 8/1988 | Hodgkin et al. | 423/DIG. 14 |
| 4,900,451 | 2/1990 | Michael et al. | 252/180 X |
| 5,338,815 | 8/1994 | Aizawa et al. | 516/102 X |
| 5,629,385 | 5/1997 | Kuo | 252/180 X |
| 5,698,512 | 12/1997 | Austin et al. | 252/180 X |
| 5,811,591 | 9/1998 | Yamamoto et al. | 568/491 |

FOREIGN PATENT DOCUMENTS

| 53-122690 | 10/1978 | Japan . |
| 59-222459 | 12/1984 | Japan . |
| 60-65003 | 4/1985 | Japan . |
| 60-238310 | 11/1985 | Japan . |
| 61-106603 | 5/1986 | Japan . |
| 2-300210 | 12/1990 | Japan . |
| 3-41104 | 2/1991 | Japan . |
| 4-211044 | 8/1992 | Japan . |
| 8-201955 | 8/1996 | Japan . |

OTHER PUBLICATIONS

J. Org. Chem., vol. 50, No. 15, 1985, Yuying et al, "Diels–Alder Reaction of 1–Azadienes. A Total Synthesis of Deoxynupharidine", p. 2725.

SYNLET, Oct. 1995, Liu et al, "Lewis Acid Rearrangement of . . . " Synthesis of N(2–amino–3–hydroxyalkyl)–substituted Amino Acid Esters, p. 1038.

J. Org. Chem. vol. 26, 1961, Reynolds et al, "Mercaptoethylation. VI. Preparation and Some Reactions of Ethyl 2–Mercaptoethylcarbonate", pp. 5125–5129.

U.S. Patent Application Serial No. 08/561,179, filed Nov. 20, 1995.

*Primary Examiner*—Richard D. Lovering
*Attorney, Agent, or Firm*—Nixon & Vanderhye P.C.

[57] ABSTRACT

A carboxylic acid polymer containing a carboxylic group and having at least one kind of bond selected from the group consisting of an amino bond, an ether bond, and a thioether bond in a side chain is prepared by polymerizing a monomer component containing a carboxylic acid monomer represented by General Formula (3):

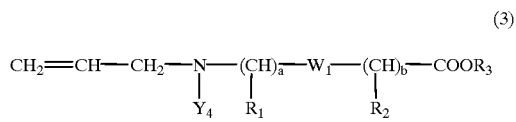

(3)

where $Y_4$ is a hydrogen atom, an allyl group, or a $-(CHR_4)_c-W_2-(CHR_5)_d-COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an $-NH-$ group, an $-S-$ group, or an $-O-$ group, and each of a, b, c, and d, independent of the others, is an integer from 0 to 6. The carboxylic acid polymer has a superior metal-scavenging ability (chelating ability) and can be suitably used, for example, as a chelating agent.

26 Claims, No Drawings

CARBOXYLATED POLYMERS, PROCESS FOR THE PRODUCTION OF THE SAME, AND GELS THEREOF

This application is a 35 U.S.C. § 371 of PCT/JP97/01669, filed May 16, 1997.

FIELD OF THE INVENTION

The present invention relates to carboxylic acid polymers, manufacturing methods thereof, and gel prepared by swelling the carboxylic acid polymers in a dispersion medium. The carboxylic acid polymers and gel are chelating and can be suitably used, for example, for recovery of metals and disposal of metal-containing waste liquids and as catalysts.

BACKGROUND OF THE INVENTION

Examples of well-known, conventional, and highly metal-chelating resins include "Duolite ES466" (product name of an ion-exchange resin available from Rohm & Haas Co.) and "Diaion CR11" (product name of an ion-exchange resin available from Mitsubishi Chemical Corp.). These resins contain an iminodiacetic acid group, and further contain a carboxylic group and an highly electron-donative nitrogen atom in a principal chain of a functional group.

However, those conventional resins undergo proton exchanges under low pH and therefore decline in metal-chelating ability. In addition, the amount of metal ions scavenged (chelated) by the resins of a unitary weight is not satisfactory. Hence there is a large demand for a resin with a superior metal-ion-scavenging ability (chelating ability).

DISCLOSURE OF THE INVENTION

In view of the problems with old arts, an object of the present invention is to offer carboxylic acid polymers with a superior metal-ion-scavenging ability (chelating ability) and gels thereof as resins with a superior metal-ion-scavenging ability (chelating ability).

The inventors of the present invention have diligently worked to accomplish the object, and as a result, have found that carboxylic acid polymers of a particular structure and gels prepared by swelling the carboxylic acid polymers in a dispersion medium exhibit a superior metal-ion-scavenging ability (chelating ability), which has led to the completion of the invention.

The present invention relates to unconventional carboxylic acid polymers containing a carboxylic group and having at least one kind of bond selected from the group consisting of an amino bond, an ether bond, and a thioether bond in a side chain.

An example of carboxylic acid polymers of the above mentioned structure is unconventional carboxylic acid polymers containing a functional group represented by General Formula (1):

$$X-(CH_2)_{n4}-S-(CH_2)_{m4}-COOH \quad (1)$$

where X is the principal segment of the carboxylic acid polymers, n4 is an integer from 0 to 6, and m4 is an integer from 0 to 6.

Another example of carboxylic acid polymers of the above mentioned structure is unconventional carboxylic acid polymers containing a functional group represented by General Formula (2):

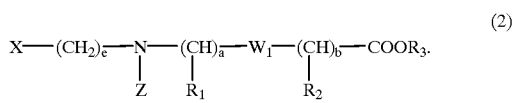

where Z is a hydrogen atom, a $-(CHR_4)_c-W_2-(CHR_5)_d-COOR_6$ group, or a $-(CH_2)_f-X$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an $-NH-$ group, an $-S-$ group, or an $-O-$ group, X is the principal segment of the carboxylic acid polymers, and each of a, b, c, d, e, and f, independent of the others, is an integer from 0 to 6.

The carboxylic acid polymers can be readily prepared by polymerizing monomer components containing a carboxylic acid monomer that contains an allylamino group and a carboxylic group and that has at least one kind of bond selected from the group consisting of an amino bond, an ether bond, and a thioether bond. An example of such a carboxylic acid monomer includes carboxylic acid monomers represented by General Formula (3):

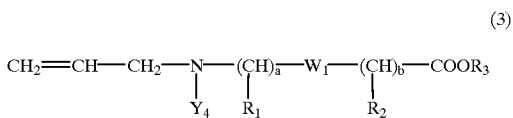

where $Y_4$ is a hydrogen atom, an allyl group, or a $-(CHR_4)_c-W_2-(CHR_5)_d-COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an $-NH-$ group, an $-S-$ group, or an $-O-$ group, and each of a, b, c, and d, independent of the others, is an integer from 0 to 6.

The carboxylic acid polymers contain not only a carboxylic group but also highly electron-donative sulfur, nitrogen, and oxygen atoms in a side chain, and consequently exhibit a superior metal-ion-scavenging ability (chelating ability). For this reason, the carboxylic acid polymers can be suitably used for separation, refinement, analysis, etc. of metal salts, such as recovery of metals and disposal of metal-containing waste liquids. Therefore, the carboxylic acid polymers can be suitably used, for example, as chelating agents. The carboxylic acid polymers, when containing a nitrogen atom, a sulfur atom, and a carboxylic group in one molecule, can stabilize metal ions in form that would not generally exist. For this reason, special catalytic effects can be expected of the carboxylic acid polymers used as catalysts in various reactions.

The carboxylic acid polymers are usable with no modification, or alternatively gels can be prepared by swelling the carboxylic acid polymers in a dispersion medium. Such gels, since prepared from the carboxylic acid polymers, are superior in metal-ion-scavenging ability (chelating ability), can be suitably used for those purposes described above, and are more widely applicable than are the carboxylic acid polymers per se.

The inventors of the present invention have diligently worked to accomplish the object, and as a result, have found that gels prepared by swelling, in a dispersion medium, carboxylic acid polymers containing a substitution group of at least one kind of structure selected from the group consisting of structures represented by following General Formulas (4) to (8) are superior in metal-ion-scavenging ability (chelating ability) and can be suitably used for those purposes described above:

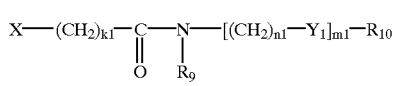
(4)

where each of $R_9$ and $R_{10}$, independent of the other, is either a hydrogen atom, a hydrocarbonate group of a carbon number from 1 to 5, or a $-(CH_2)_{p1}-X$ group, p1 is an integer from 0 to 6, k1 is an integer from 0 to 6, m1 is an integer from 0 to 6, n1 is an integer from 0 to 6, Y1 is an $-O-$ group, an $-S-$ group, or an $-NR_{11}-$ group, $R_{11}$ is a hydrogen atom or a hydrocarbon of a carbon number from 1 to 5, and X is the principal segment of the carboxylic acid polymers;

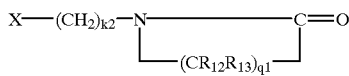
(5)

where each of $R_{12}$ and $R_{13}$, independent of the other, is either a hydrogen atom or a hydrocarbonate group of a carbon number from 1 to 5, k2 is an integer from 0 to 6, and q1 is an integer from 3 to 6;

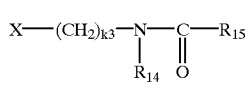
(6)

where $R_{14}$ is a hydrogen atom, a hydrocarbonate group of a carbon number from 1 to 5, or a $-(CH_2)_{p2}-X$ group, p2 is an integer from 0 to 6, $R_{15}$ is a hydrocarbonate group of a carbon number from 1 to 5 or a $-(CH_2)_{p3}-X$ group, p3 is an integer from 0 to 6, k3 is an integer from 0 to 6, and X is the principal segment of the carboxylic acid polymers;

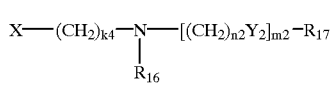
(7)

where $R_{16}$ is a hydrogen atom, a hydrocarbonate group of a carbon number from 1 to 5, or a $-(CH_2)_{p4}-X$ group, p4 is an integer from 0 to 6, k4 is an integer from 0 to 6, n2 is an integer from 0 to 6, Y2 is an $-O-$ group, an $-S-$ group, an $-NR_{18}-$ group, or a $-CH_2-$ group, $R_{18}$ is a hydrogen atom or a hydrocarbonate group of a carbon number from 1 to 5, X is the principal segment of the carboxylic acid polymers, m2 is an integer from 0 to 6, $R_{17}$ is a hydrogen atom, a hydrocarbonate group of a carbon number from 1 to 5, a $-(CH_2)_{p5}-X$ group, or a Brønsted acid residual group when $m_2 \neq 0$, and is a hydrogen atom, a hydrocarbonate group of a carbon number from 1 to 5, or a $-(CH_2)_{p5}-X$ group when $m_2=0$, and p5 is an integer from 0 to 6; and

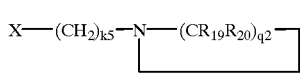
(8)

where each of $R_{19}$ and $R_{20}$, independent of the other, is either a hydrogen atom or a hydrocarbonate group of a carbon number from 1 to 5, k5 is an integer from 0 to 6, q2 is an integer from 4 to 7, and X is the principal segment of the carboxylic acid polymers.

The inventors of the present invention have also found that gels prepared by swelling, in a dispersion medium, carboxylic acid polymers prepared by copolymerization of an unsaturated monomer (A) containing a carboxylic group and an unsaturated monomer (B) containing an amino group and/or an amide group are superior in metal-ion-scavenging ability (chelating ability) and can be suitably used for those purposes described above.

As described so far, the carboxylic acid polymers and gels in accordance with the present invention are superior in metal-ion-scavenging ability (chelating ability). Therefore, a chelating agent containing at least one kind of such carboxylic acid polymers and gels are superior in metal-ion-scavenging ability (chelating ability) and can be suitably used for those purposes described above.

The following description will discuss the present invention in more detail.

The carboxylic acid polymers are compounds containing a carboxylic group and having at least one kind of bond selected from the group consisting of an amino bond, an ether bond, and a thioether bond in a side chain. In the present invention, the carboxylic groups include substituted carboxylic groups derived from the carboxylic groups by replacing a hydrogen atom with another functional group.

The carboxylic acid polymers are not limited in any particular manner as long as they are compounds containing a sulfur atom and a carboxylic group in a side chain. An example of such carboxylic acid polymers is compounds containing a functional group of a structure represented by either General Formula (1) or General Formula (2):

(1)

where X is the principal segment of the carboxylic acid polymers, n4 is an integer from 0 to 6, and m4 is an integer from 0 to 6; and

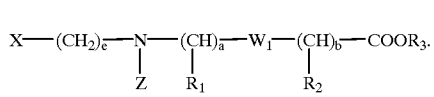
(2)

where Z is a hydrogen atom, a $-(CHR_4)_c-W_2-(CHR_5)_d-COOR_6$ group, or a $-(CH_2)_f-X$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an $-NH-$ group, an $-S-$ group, or an $-O-$ group, X is the principal segment of the carboxylic acid polymers, and each of a, b, c, d, e, and f, independent of the others, is an integer from 0 to 6. Here, the "principal segment of a carboxylic acid polymer" refers to the principal chain of that carboxylic acid polymer, and may be a homopolymerized monomer containing a carboxylic group (e.g. the carboxylic acid monomer above) or alternatively a monomer, containing a carboxylic group, which is copolymerized with another monomer that is copolymerizable with that monomer containing a carboxylic group. Especially preferred among the carboxylic acid polymers represented by General Formula (2) are compounds such that each of the substitution groups depicted as $R_1$, $R_2$, $R_4$, and $R_5$, independent of the others, is either a hydrogen atom or an alkyl group of a carbon number from 1 to 3, and the substitution groups depicted as $R_3$ and $R_6$ are hydrogen atoms.

The manufacturing methods of the carboxylic acid polymers in accordance with the present invention is not limited in any particular manner. Examples of such manufacturing methods include the following two methods.

First Method: React polymer (A) containing a primary or secondary alkyl halogen, sulfonate ester, etc. in a side chain with various sulfurizing agents. Furnish an —SH group to an end of polymer (A) by hydrolysis, or reduction with a processing agent, of an intermediate product resulting from that reaction. Next, add an ethylenic unsaturated carboxylic acid, such as acrylic acid or methacrylic acid, to polymer (A).

Second Method: Polymerize a monomer component containing a carboxylic acid monomer that contains an allyl amino group and a carboxylic group and that has at least one kind of bond selected from the group consisting of an amino bond, an ether bond, and a thioether bond.

The first method is suitable, for example, for the manufacture of a carboxylic acid polymer containing a functional group of a structure represented by General Formula (1). The second method is suitable, for example, for the manufacture of a carboxylic acid polymer containing a functional group of a structure represented by General Formula (2).

The sulfurizing agents used as a material in the first method are not limited in any particular manner. Examples of such sulfurizing agents include compounds represented by formulas: $(NH_2)_2C=S$,

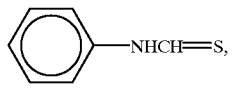

NaHS, and $Na_2S_2O_3$. The sulfurizing agents may be used singly or if necessary in a proper combination of two or more.

The processing agent is not limited in any particular manner. Examples of such a processing agent include NaOH, HCl, H$^+$, and LiAlH$_4$. The processing agent may be used singly or if necessary in a proper combination of two or more.

Conditions for the manufacture of a carboxylic acid polymer according to the first method are not limited in any particular manner, being set properly depending upon, for example, desired properties of the carboxylic acid polymer. Since the resultant carboxylic acid polymer has not only a carboxylic group but also highly electron-donative sulfur, nitrogen, and oxygen atoms in a side chain, it is superior in chelating, and can be suitably used for a variety of purposes such as recovery of metals and disposal of metal-containing waste liquids and as a catalyst.

The carboxylic acid monomer used as a material in the second method is an unconventional carboxylic acid monomer in accordance with the present invention. The carboxylic acid monomer is a compound that contains an allyl amino group and a carboxylic group and that has at least one kind of bond selected from the group consisting of an amino bond, an ether bond, and a thioether bond.

Note that in the present invention, the aforementioned carboxylic groups include substituted carboxylic groups derived from the carboxylic groups by replacing a hydrogen atom with another functional group, and that the allylamino groups include substituted allylamino groups derived from the allylamino groups by replacing a hydrogen atom bonded to a nitrogen atom with another functional group.

The carboxylic acid monomer is not limited in any particular manner as long as it meets the above-mentioned conditions. An example of such a carboxylic acid monomer includes compounds represented by General Formula (3):

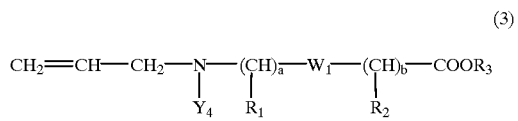

(3)

where $Y_4$ is a hydrogen atom, an allyl group, or a —$(CHR_4)_c$—$W_2$—$(CHR_5)_d$—$COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an —NH— group, an —S— group, or an —O— group, and each of a, b, c, and e, independent of the others, is an integer from 0 to 6.

Preferred among these compounds are compounds such that the substitution group depicted as $Y_4$ is a hydrogen atom, an allyl group, or a —$(CHR_4)_c$—$W_2$—$(CHR_5)_d$—$COOR_6$ group, the substitution groups depicted as $R_3$ and $R_6$ are hydrogen atoms, and the repetition units depicted as a, b, c, and d equal 2. Especially preferred among them, as represented by formulas (9) to (11), are compounds such that the substitution groups depicted as $R_1$, $R_2$, $R_3$, $R_4$, $R_5$, and $R_6$ are hydrogen atoms, and the repetition units depicted as a, b, c, and d equal 2:

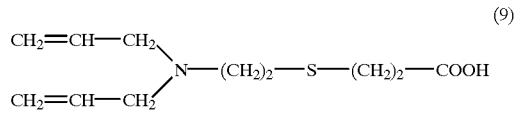

(9)

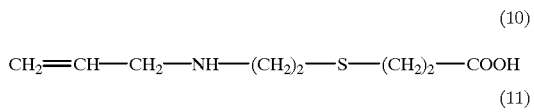

(10)

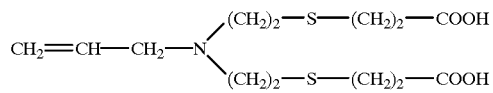

(11)

The most preferred among these compounds are those represented by formula (9).

The aforementioned carboxylic acid monomers are readily prepared from materials generally available by a manufacturing method constituted by simple processes. The carboxylic acid monomers have no particular conditions imposed on the manufacturing method thereof, being able to be manufactured by various methods. Examples of such methods of readily preparing a desired carboxylic acid polymer include reacting (meth)acrylic acid with a compound represented by General Formula (12):

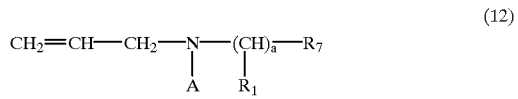

(12)

where A is a hydrogen atom, an allyl group, or a —$(CHR_4)_c$—$R_8$ group, each of $R_1$ and $R_4$, independent of the other, is either a hydrogen atom or an alkyl group of a carbon number from 1 to 6, each of $R_7$ and $R_8$, independent of the other, is either an —SH group, an —OH group, or an —NH$_2$ group, and each of a and c, independent of the other, is an integer from 0 to 6.

The compounds represented by General Formula (12) are not limited in any particular manner, being such that in General Formula (12) the substitution group depicted as A is constituted by a hydrogen atom, an allyl group, or a —(CHR$_4$)$_c$—R$_8$ group, the substitution groups depicted as R$_1$ and R$_4$ are, each independent of the other, constituted by a hydrogen atom or an alkyl group of a carbon number from 1 to 6, the substitution groups depicted as R$_7$ and R$_8$ are, each independent of the other, constituted by an —SH group, an —OH group, or an —NH$_2$ group, the repetition unit depicted as a is an integer from 0 to 6, and the repetition unit depicted as c is an integer from 0 to 6.

Examples of the compounds represented by General Formula (12) include: 2-(allylaminoethanethiol) represented by formula (13), 2-(allyl-(2-mercapt ethyl) aminoethanethiol represented by formula (14), 2-diallylaminoethanethiol represented by formula (15), and adiallylaminoethanol represented by formula (16):

(13)

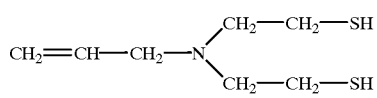

(14)

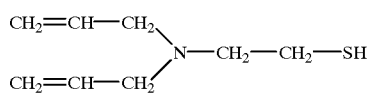

(15)

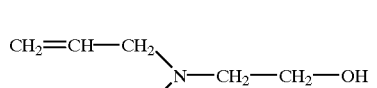

(16)

The compounds represented by formula (12) may be used singly or if necessary in a proper combination of two or more.

The compounds represented by formula (12) have no particular conditions imposed on the manufacturing method thereof, being able to be manufactured by various conventionally well-known methods. An example is found on page 5125 and its following pages of J. Org. Chem 26, 1961, where compounds such as 2-diallylaminoethanethiol are synthesized using ethyl-2-hydroxy ethylthiocarbonate as either a primary or secondary mercapt ethylificating agent.

The method of separating out the compounds represented by formula (12) in the reaction above is not limited in any particular manner. Examples of such methods include conventionally well-known various methods such as distillation.

A solvent may be added, when necessary, to the reaction system of (meth)acrylic acid with a compound represented by formula (12). The solvent is not limited in any particular manner as long as it does not interfere with the reaction. Examples of such a solvent include organic solvents such as dioxane and tetrahydrofuran. The amount of the solvent used is not limited in any particular manner.

The (meth)acrylic acid may be reacted at any temperature with a compound represented by formula (12). However the reaction temperature is preferably specified in a range from 0° C. to 200° C. To increase the yield of the monomer, the reaction temperature is preferably specified in a range from 10° C. to 100° C. and more preferably in a range from 20° C. to 80° C. Reaction temperatures below 0° C. are not preferable because the reaction takes too much time and declines in efficiency. The (meth)acrylic acid and allylamines, which are starting materials, and the carboxylic acid monomer, which is a product, contain a vinyl group in molecules thereof and therefore can be readily polymerized. So, reaction temperatures above 200° C. are not preferable because the polymerization of these compounds cannot be terminated. The reaction time is specified properly depending upon the reaction temperature, the reaction product, and the kinds, combinations, and amounts of (meth)acrylic acid and the solvents used, so as to complete the reaction. The reaction pressure is not limited in any particular manner, being either normal (atmospheric) pressure, decreased pressure, or increased pressure.

As mentioned so far, the carboxylic acid monomer is a compound that contains an allylamino group and a carboxylic group and that has at least one kind of bond selected from the group consisting of an amino bond, an ether bond, and a thioether bond. Such a carboxylic acid monomer has a structure shown in General Formulas (1) and (9) through (11), as examples. The carboxylic acid monomer is readily available by reacting (meth)acrylic acid with a compound represented by General Formula (12).

As mentioned so far, the carboxylic acid polymers in accordance with the present invention are readily prepared by polymerizing a monomer component containing the above-mentioned carboxylic acid monomer. The monomer component may contain, if necessary, an other monomer that can be copolymerized with the carboxylic acid monomer. Examples of such another monomer include monomers containing a carboxylic group such as (meth)acylic acid, maleic acid, or fumaric acid, esters thereof, styrene, vinylpyridine, and allylamines. However, the other monomers are not limited in any particular manner. The other monomers may be used singly or if necessary in a proper combination of two or more. Preferred among the other monomers is (meth)acrylic acid. The amount of the other monomer added to the carboxylic acid monomer is not limited in any particular manner.

The manufacturing method of the carboxylic acid polymers, i.e. the polymerization method of the monomer component that includes the carboxylic acid monomer, is not limited in any particular manner, specifically being a solution polymerization method, a suspension polymerization method, a water-in-oil phase suspension polymerization method, and other various conventionally well-known methods. The solvent used for the polymerization of the monomer component is not limited in any particular manner, specifically being water, toluene, and cyclohexane. The amount of the solvent used is not limited in any particular manner either. The suspension agent used for the suspension polymerization is not limited in any particular manner, specifically being gelatin, dextrin, and polyvinyl alcohol. The amount of the suspension polymerization used is not limited in any particular manner either.

A polymerization initiator may be used for the polymerization of the monomer component: namely, as examples, a radical polymerization initiator such as a peroxide such as hydrogen peroxide, benzoyl peroxide, or cumene hydroperoxide; an azo compound such as 2,2'-azobis isobutyronitrile or 2,2'-azobis-(2-amidinopropane) dihydrochloride; a persulfate salt such as ammonium persulfate, sodium persulfate, or potassium persulfate. The polymerization initiators may be used singly or if necessary in a proper combination of two or more. Alternatively, radioactive, electron or ultraviolet rays may be used instead of using the polymerization initiator. A further alternative is to use both the polymerization initiator and the radioactive, electron or ultraviolet rays. The amount of the polymerization initiator used is not limited in any particular manner.

A crosslinking agent may be used for the polymerization of the monomer component if necessary. Such crosslinking agents are not limited in any particular manner, specifically being trimethylolpropane triacrylate and divinylbenzene. The crosslinking agents may be used singly or if necessary in a proper combination of two or more. The use of the crosslinking agent in the polymerization reaction makes it possible to control the crosslinking densities of the resultant carboxylic acid polymers. The amount of the crosslinking agent used is not limited in any particular manner, being specified properly depending upon, for example, the kinds of the monomer component and crosslinking agent used, and desired crosslinking density.

The reaction temperature for the polymerization is not limited in any particular manner, being specified properly depending upon, for example, the kinds of the monomer component and solvent. The reaction temperature is preferably specified in a range from 50° C. to 120° C., and more preferably in a range from 60° C. to 100° C. The reaction time is not limited in any particular manner, being specified properly depending upon the reaction temperature, and the kinds, combinations, and amounts used of the monomer component, polymerization initiator, solvent, etc., so as to complete the polymerization reaction. The reaction pressure is not limited in any particular manner, being either normal (atmospheric) pressure, decreased pressure, or increased pressure.

The carboxylic acid polymers are readily prepared by, after the polymerization reaction, filtering, sufficiently washing in a solvent, and then drying by a commonly used method such as an evaporator or depressurization drying.

The carboxylic acid polymers thus obtained contain not only a carboxylic group but also highly electron-donative nitrogen, sulfur, and oxygen atoms in a side chain, and consequently are superior in metal-ion-scavenging ability (chelating ability) even under low pH conditions (pH=3 or less), and exhibits as large a metal-ion-scavenging amount (chelating amount) per unitary volume thereof as 10 mmol per 1 cc.

Therefore, the carboxylic acid polymers can be suitably used, for example, for recovery of metals and disposal of metal-containing waste liquids. Consequently, the aforementioned carboxylic acid polymers can be suitably used as, for example, chelating agents.

The carboxylic acid polymers, when containing a nitrogen atom, a sulfur atom, and a carboxylic group in one molecule, can stabilize metal ions in form that would not generally exist.

For this reason, special catalytic effects can be expected of the carboxylic acid polymers used as catalysts in various reactions.

The carboxylic acid polymers in accordance with the present invention may be used as catalysts with no modification or with a metal ion being chelated.

The carboxylic acid polymers in accordance with the present invention can be used with no modification as catalysts in Knoevenagel condensation reaction, and can be suitably used especially as catalysts in a reaction of, for example, hydroxyalkanal by holding a metal. The metal used herein is not limited in any particular manner. Examples of such a metal include copper, lead, nickel, zinc, iron, cobalt, chromium, manganese, bismuth, tin, antimony, and alkaline earth metals. The carboxylic acid polymers holding a metal are suitably used especially as catalysts in selective synthesis of acrylic acid esters.

The amount of the metal to the carboxylic acid polymer holding that metal is limited in any particular manner, being specified properly depending upon the kind of the carboxylic acid polymer and the kind of the synthesis reaction in which the catalyst is used.

For example, when a carboxylic acid polymer containing a functional group of a structure represented by General Formula (2) is used as a catalyst in a synthesis reaction of hydroxyalkanal, the amount of the metal held by the carboxylic acid polymer is preferably in a range from 0.001 weight % to 10 weight %, more preferably in a range from 0.01 weight % to 5 weight %, and even more preferably in a range from 0.01 weight % to 1 weight %. If the amount of the metal held is less than 0.001 weight %, expected results may not obtained from the carboxylic acid polymer holding the metal. By contrast, if the amount of the metal held is more than 10 weight %, the yield of hydroxyalkanal may decline. The word, "hold", herein is not limited to chelating, but may include salt formation, absorption, clathrate formation, etc. The metal held may be either a metal or ions. The ions may be an oxide, halogenide, sulfide, etc.

The method of letting the carboxylic acid polymers hold a metal is not limited in any particular manner. A conventional method may be employed. A metal, e.g. lead, can be hold by a carboxylic acid polymer by the following process: Immerse the carboxylic acid polymer in a water solution in which a predetermined amount of a lead compound such as lead sulfate or lead acetate is dissolved, and then stir the mixture under predetermined conditions for cation exchange. Thereafter, for example, filter the mixture to separate out the carboxylic acid polymer and then wash in water.

The carboxylic acid polymers, containing a nitrogen atom, a sulfur atom, and a carboxylic group in one molecule, are expected to possess special catalytic effects even without chelating a metal, due to acid-base interactive effects.

As described above, the carboxylic acid polymers possess a superior metal-ion-scavenging ability (chelating ability) and can be suitably used for a variety of purposes with no modification or with a metal ion being chelated.

As mentioned above, the carboxylic acid polymers can be either used as chelating agents with no modification or used as gels by swelling the carboxylic acid polymers in a dispersion medium.

The gels are jelly-like solid substances formed from the carboxylic acid polymers swollen in a dispersion medium and thereby taking a three-dimensional reticular structure.

The dispersion medium is not limited in any particular manner, preferably being water, methanol, etc. The manufacturing method of the gels are not limited in any particular manner For example, the gels are obtained by immersing the carboxylic acid polymers in the dispersion medium. No particular conditions are imposed on the immersion of the carboxylic acid polymers in the dispersion medium. The swelling ratio of the gels, or in other words, the amount of the dispersion medium contained, is not limited in any particular manner, 1 g of a carboxylic acid polymer typically absorbing 4 g to 6 g of water.

The gels, containing a carboxylic acid polymer, are superior especially in metal-ion-scavenging ability (chelating ability). In other words, since the carboxylic acid polymers exhibit a superior metal-chelating ability even under low pH conditions and a large metal-ion-scavenging amount (chelating amount) per unitary volume thereof, the gels formed by swelling the carboxylic acid polymers in the dispersion medium also exhibit a superior metal-chelating ability even under low pH conditions and a large metal-ion-scavenging amount (chelating amount) per unitary volume thereof. Therefore, the gels can also be suitably used, for example, for recovery of metals and disposal of metal-containing waste liquids.

The carboxylic acid polymers, when containing a nitrogen atom, a sulfur atom, and a carboxylic group in one molecule, can stabilize metal ions in form that would not generally exist. For this reason, special catalytic effects can be expected of the carboxylic acid polymers used as catalysts in various reactions.

The gels may be used as catalysts with no modification to the carboxylic acid polymers or with a modification to letting the carboxylic acid polymers hold a metal.

The gels in accordance with the present invention can be used as catalysts in Knoevenagel condensation reaction by using the carboxylic acid polymers with no modification, and can be suitably used especially as catalysts in a synthesis reaction of, for example, hydroxyalkanal with metal. The gels are also suitably used especially as catalysts in selective synthesis of acrylic acid esters with metal.

The amount of the metal to the carboxylic acid polymer holding that metal is not limited in any particular manner, being specified properly depending upon the kind of the carboxylic acid polymer and the kind of the synthesis reaction in which the catalyst is used.

For example, when a carboxylic acid polymer containing a functional group of a structure represented by General Formula (2) is used as a catalyst in a synthesis reaction of hydroxyalkanal, the amount of the metal held by the carboxylic acid polymer is preferably in a range from 0.001 weight % to 10 weight %, more preferably in a range from 0.01 weight % to 5 weight %, and even more preferably in a range from 0.01 weight % to 1 weight %.

The carboxylic acid polymers, containing a nitrogen atom, a sulfur atom, and a carboxylic group in one molecule, are expected to possess special catalytic effects even without chelating a metal, due to acid-base interactive effects. Consequently, the gels containing the carboxylic acid polymers are also suitably used as catalysts even without chelating a metal.

Alternatively, the gels, since prepared by swelling the carboxylic acid polymers in a dispersion medium, are more widely applicable than are the carboxylic acid polymers per se. For example, the three-dimensional reticular structure of the gels imparts molecule-sieving effects thereto, and allows the gels to be suitably used, for example, for refinement of sugar and as absorbing agents and filtering agents for separating a mixture of gasses and liquids.

The gels are highly responsive to heat and reversible in thermal expansion. Therefore a change in volume of the gels at high temperatures can be converted to pressure and thereby applied, as an example, for an actuator. The gels are also highly responsive to pH, being capable of altering their form (crosslinking density) according to acidity or alkalinity. Therefore, the gels can be suitably used for, as an example, a so-called drug delivery system according to which the gels containing a desired compound such as pharmaceuticals release the same in a particular pH environment such as in a human body.

As described above, the carboxylic acid polymers and the gels thereof are superior in metal-ion-scavenging ability (chelating ability), and can be suitably used as chelating agents, as an example. When the carboxylic acid polymers or the gels thereof are used as chelating agents, those chelating agents may contain a conventional, well-known chelating agent and other additives, in addition to the carboxylic acid polymers.

That is, a chelating agent in accordance with the present invention is arranged to contain a carboxylic acid polymer containing a carboxylic group and having at least one kind of bond selected from the group consisting of an amino bond, an ether bond, and a thioether bond in a side chain.

The chelating agent in accordance with the present invention, by way of the inclusion of the carboxylic acid polymer, exhibits a superior metal-ion-scavenging ability (chelating ability), a superior metal-chelating ability even under low pH conditions, and a large metal-ion-scavenging amount (chelating amount) per unitary volume thereof. Therefore, the chelating agent can be suitably used for separation, refinement, analysis, etc. of metal salts, such as recovery of metals and disposal of metal-containing waste liquids.

Examples of other carboxylic acid polymers in accordance with the present invention and gels thereof, i.e. chelating carboxylic acid polymers and gels thereof, include the carboxylic acid polymers containing a substitution group of at least one kind of structure selected from the group consisting of structures represented by following General Formulas (4) to (8), and also include the gels prepared by swelling the carboxylic acid polymers in a dispersion medium:

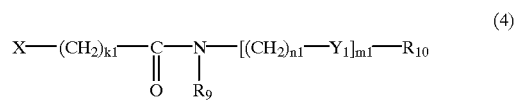

(4)

where each of $R_9$ and $R_{10}$, independent of the other, is either a hydrogen atom, a hydrocarbonate group of a carbon number from 1 to 5, or a —$(CH_2)_{p1}$—X group, p1 is an integer from 0 to 6, k1 is an integer from 0 to 6, m1 is an integer from 0 to 6, n1 is an integer from 0 to 6, Y1 is an —O— group, an —S— group, or an —$NR_{11}$— group, $R_{11}$ is a hydrogen atom or a hydrocarbon of a carbon number from 1 to 5, and X is the principal segment of the carboxylic acid polymers;

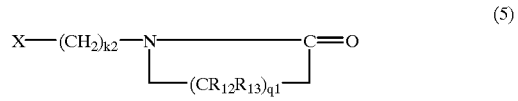

(5)

where each of $R_{12}$ and $R_{13}$, independent of the other, is either a hydrogen atom or a hydrocarbonate group of a carbon number from 1 to 5, k2 is an integer from 0 to 6, and q1 is an integer from 3 to 6;

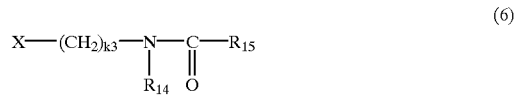

(6)

where $R_{14}$ is a hydrogen atom, a hydrocarbonate group of a carbon number from 1 to 5, or a —$(CH_2)_{p2}$—X group, p2 is an integer from 0 to 6, $R_{15}$ is a hydrocarbonate group of a carbon number from 1 to 5 or a —$(CH_2)_{p3}$—X group, p3 is an integer from 0 to 6, k3 is an integer from 0 to 6, and X is the principal segment of the carboxylic acid polymers;

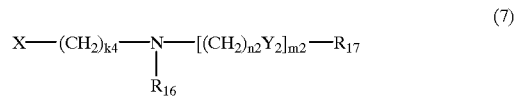

(7)

where $R_{16}$ is a hydrogen atom, a hydrocarbonate group of a carbon number from 1 to 5, or a —$(CH_2)_{p4}$—X group, p4 is an integer from 0 to 6, k4 is an integer from 0 to 6, n2 is an integer from 0 to 6, Y2 is an —O— group, an —S— group, an —$NR_{18}$— group, or a —$CH_2$— group, $R_{18}$ is a hydrogen atom or a hydrocarbonate group of a carbon number from 1 to 5, X is the principal segment of the carboxylic acid polymers, m2 is an integer from 0 to 6, $R_{17}$ is a hydrogen atom, a hydrocarbonate group of a carbon number from 1 to 5, a $—(CH_2)_{p5}—X$ group, or a Brønsted acid residual group when $m_2 \neq 0$, and is a hydrogen atom, a hydrocarbonate group of a carbon number from 1 to 5, or a $—(CH_2)_{p5}—X$ group when $m_2=0$, and p5 is an integer from 0 to 6; and

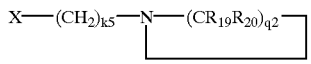
(8)

where each of $R_{19}$ and $R_{20}$, independent of the other, is either a hydrogen atom or a hydrocarbonate group of a carbon number from 1 to 5, k5 is an integer from 0 to 6, q2 is an integer from 4 to 7, and X is the principal segment of the carboxylic acid polymers. Examples further include carboxylic acid polymers prepared by copolymerization of the unsaturated monomer (A) containing a carboxylic group and the unsaturated monomer (B) containing an amino group and/or an amide group, and gels prepared by swelling those carboxylic acid polymers in a dispersion medium.

In General Formulas (4) to (8), the hydrocarbonate group of a carbon number from 1 to 5 refers to a methyl, ethyl, propyl, butyl, or amyl group. The segment depicted as X in the formulas refers to the principal segment of the carboxylic acid polymer. The carboxylic acid polymer refers to a polymer containing a large number of free carboxyl groups. The principal segment of the carboxylic acid polymer may be a homopolymerized monomer containing a carboxylic group or alternatively a monomer, containing a carboxylic group, which is copolymerized with another monomer that is copolymerizable with that monomer containing a carboxylic group (the latter type of monomer will be referred to as a copolymeric monomer for convenience).

The monomer containing a carboxylic group is not limited in any particular manner, typically being a carboxylic acid such as (meth)acylic acid, maleic acid, or fumaric acid. Those monomers containing a carboxylic group may be used singly or if necessary in a proper combination of two or more.

The copolymeric monomer is not limited in any particular manner, being a monomer containing an olefin group. Examples of the copolymeric monomer include the monomers containing a carboxylic group, esters thereof, styrenes thereof, and vinylpyridines thereof. The copolymeric monomer may include a functional group other than a carboxyl group, such as a phosphoric acid group, a sulfonic acid group, or a hydroxyl group. The copolymeric monomer may be used singly or if necessary in a proper combination of two or more.

Preferred among the carboxylic acid polymers containing an amide group of a structure represented by General Formula (4) are those with a nitrogen or sulfur atom being contained in the bivalent substitution group depicted as Y1. Especially preferred are those with a sulfur atom. Preferred among the carboxylic acid polymers containing an amide group of a structure represented by General Formula (5) are those with the repetition unit depicted as q1 being equal to 3.

Preferred among the carboxylic acid polymers containing an amino group of a structure represented by General Formula (7) are those with a nitrogen or sulfur atom being contained in the bivalent substitution group depicted as Y2. Especially preferred are those with a sulfur atom. The Brønsted acid residual group in General Formula (7) refers to a proton-donating group such as a carboxylic group, a phosphoric acid group, a phosphorous acid group, a sulfonic acid group, or a hydroxyl group, and in the present invention refers also to a hydrocarbonate group of a carbon number from 1 to 5 with the proton-donating group substituted for at least one of the hydrogen atoms thereof.

A preferred example of the carboxylic acid polymer (the principal segment) is a (meth)acrylic acid polymer. If the (meth)acrylic acid polymer contains an amide group, a (meth)acrylic acid-(meth)acrylamides copolymer and a (meth)acrylic acid-vinylpyrrolidones copolymer are preferred. The (meth)acrylic acid-(meth)acrylamides copolymer is not limited in any particular manner, specifically being a (meth)acrylic acid-(meth)acrylamide copolymer, a (meth)acrylic acid-N,N-dimethyl(meth) acrylamide copolymer, a (meth)acrylic acid-N-isopropyl (meth) acrylamide copolymer, or a (meth)acrylic acid-N,N-dimethyl aminopropyl (meth)acrylamide copolymer as examples. The (meth)acrylic acid-vinylpyrrolidones copolymer is not limited in any particular manner, specifically being a (meth)acrylic acid-N-vinylpyrrolidones copolymer as an example.

The (meth)acrylic acid polymer containing an amino group is not limited in any particular manner, specifically being a (meth)acrylic acid-2-vinylpyridines copolymer, a (meth)acrylic acid-4-vinylpyridines copolymer, a (meth)acrylic acid-N-vinyl carbazoles copolymer, a (meth)acrylic acid-N-monoallylamines copolymer, a (meth)acrylic acid-N,N-diallylamines copolymer, a (meth)acrylic acid-N,N,N-triallylamines copolymer, and a (meth)acrylic acid-4-(N,N-dialkylamino) alkylstyrenes copolymer as examples.

The manufacturing method of the carboxylic acid polymers is not limited in any particular manner. Neither are the conditions for the manufacture thereof.

The carboxylic acid polymers prepared by copolymerization of the unsaturated monomers (A) and (B) is not limited in any particular manner. The unsaturated monomer (A) is not limited in any particular manner, specifically being monomers containing the aforementioned carboxylic group as examples.

The unsaturated monomer (B) is not limited in any particular manner, typically being a nitrogen-containing unsaturated compound such as vinylpyridines, N-vinyl carbazoles, allylamines, 4-(N,N-dialkylamino) alkylstyrenes, 6-(N-propenylamino)-4-thiahexane acid, or 6-(N,N-dipropenylamino)-4-thiahexane acid.

In the unsaturated monomer (B), a substitution group represented by General Formula (17) may be bonded to a nitrogen atom(s) constituting the amino group and/or the amide group:

(17)

where n3 is an integer from 0 to 6, Y3 is an —O— group, an —S— group, an —NR$_{22}$— group, or a —CH$_2$— group, $R_{22}$ is a hydrogen atom or a hydrocarbonate group of a carbon number from 1 to 5, m3 is an integer from 0 to 6, $R_{21}$ is a hydrogen atom, a hydrocarbonate group of a carbon number from 1 to 5, or a Brønsted acid residual group when $m_3 \neq 0$, and is a hydrogen atom, or a hydrocarbonate group of a carbon number from 1 to 5 when $m_3=0$ In addition, the carboxylic acid polymers may be prepared by copolymerization of the unsaturated monomer (A), the unsaturated monomer (B), and the copolymeric monomer. The Brønsted acid residual group in General Formula (17) refers to a proton-donating group such as a carboxylic group, a phosphoric acid group, a phosphorous acid group, a sulfonic acid group, or a hydroxyl group, and in the present invention refers also to a hydrocarbonate group of a carbon number from 1 to 5 with the proton-donating group substituted for at least one of the hydrogen atoms thereof.

The aforementioned vinylpyridine is not limited in any particular manner, specifically being a 2-vinylpyridine and a 4-vinylpyridine as examples. Examples of allylamines include N-monoallylamines, N,N-diallylamines, and N,N,N-triallylamines. Preferred among the allylamines are N-monoallylamine, N,N-diallylamine, and N,N,N-triallylamine. An example of 4-(N,N-dialkylamino) alkylstyrene is a compound represented by General Formula (18):

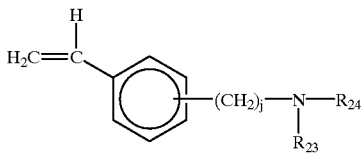

(18)

where each of $R_{23}$ and $R_{24}$, independent of the other, is either a hydrogen atom or a hydrocarbonate group of a carbon number from 1 to 5, and j is an integer from 0 to 5. In General Formula (18), the hydrocarbonate group of a carbon number from 1 to 5 refers to a methyl, ethyl, propyl, butyl, or amyl group. Preferred among the 4-(N,N-dialkylamino) alkylstyrenes represented by General Formula (18) are those with the repetition unit depicted as j being equal to 1 to 3, since they react well with the unsaturated monomer (A), and carboxylic acid polymers formed from them, e.g. catalysts, react well. An example of the 4-(N,N-dialkylamino) alkylstyrenes represented by General Formula (18) is 4-(N,N-dimethyl amino) ethyl styrene.

Preferred among the carboxylic acid polymers prepared by copolymerization of the unsaturated monomers (A) and (B) are those with the unsaturated monomer (A) being (meth) acrylic acid and the unsaturated monomer (B) being an allylamine, since they are superior in metal-ion-scavenging ability (chelating ability) and resultant gels are especially superior in metal-ion-scavenging ability (chelating ability).

The manufacturing method of the carboxylic acid polymers, i.e. the polymerization method of the monomer component that includes the unsaturated monomers (A) and (B), is not limited in any particular manner, being a solution polymerization method, a suspension polymerization method, a water-in-oil phase suspension polymerization method, and other various conventionally well-known methods as examples. The solvent used for the polymerization of the monomer component and the suspension agent used for the suspension polymerization are not limited in any particular manner, being a solvent and suspension agent similar to those listed for the polymerization of the monomer component that includes the carboxylic acid monomer as examples. The amounts of the solvent and the suspension agent used are not limited in any particular manner either.

A polymerization initiator may be used for the polymerization of the monomer component. The polymerization initiator is not limited in any particular manner, being a polymerization initiator similar to those listed for the polymerization of the monomer component that includes the carboxylic acid monomer as examples. Alternatively, radioactive, electron or ultraviolet rays may be used instead of using the polymerization initiator. A further alternative is to use both the polymerization initiator and the radioactive, electron or ultraviolet rays.

A crosslinking agent may be used for the polymerization of the monomer component, if necessary, to control the crosslinking densities of the resultant carboxylic acid polymers. Such a crosslinking agent is not limited in any particular manner, being a crosslinking agent similar to those listed for the polymerization of the monomer component that includes the carboxylic acid monomer as examples. The amount of the crosslinking agent used is not limited in any particular manner, being specified properly depending upon, for example, the kinds of the monomer component and crosslinking agent used, and desired crosslinking density.

The reaction temperature for the polymerization is not limited in any particular manner, being specified properly depending upon, for example, the kinds of the monomer component and solvent. The reaction temperature is preferably specified in a range from 50° C. to 120° C., and more preferably in a range from 60° C. to 100° C. The reaction time is not limited in any particular manner, being specified properly depending upon the reaction temperature, and the kinds, combinations, and amounts used of the monomer component, polymerization initiator, solvent, etc., so as to complete the polymerization reaction. The reaction pressure is not limited in any particular manner, being either normal (atmospheric) pressure, decreased pressure, or increased pressure.

The carboxylic acid polymers are readily prepared by, after the polymerization reaction, filtering, sufficiently washing in a solvent, and then drying by a commonly used method such as an evaporator or depressurization drying.

Gels can be readily obtained from the carboxylic acid polymers by swelling them in a dispersion medium. The gels are jelly-like solid substances formed from the carboxylic acid polymers swollen in a dispersion medium and thereby taking a three-dimensional reticular structure.

Similarly to the manufacture of the gels, the dispersion medium is not limited in any particular manner, preferably being water, methanol, etc. The manufacturing method of the gels is not limited in any particular manner. For example, the gels are readily obtained by immersing the corresponding carboxylic acid polymers in the dispersion medium. No particular conditions are imposed on the immersion of the carboxylic acid polymers in the dispersion medium. The swelling ratio of the gels, or in other words, the amount of the dispersion medium contained, is not limited in any particular manner, 1 g of a carboxylic acid polymer typically absorbing 4 g to 6 g of water.

The gels are superior in chelating ability even under low pH conditions, and exhibits a large metal-ion-scavenging amount (chelating amount) per unitary volume thereof, as high as 10 mmol per 1 cc. Besides, the gels in a non-protonic solvent exhibits an acid strength 10 to 100 times that of the gels in a protonic solvent. Therefore, the gels can be suitably used, for example, for recovery of metals and disposal of metal-containing waste liquids, and also as various process catalysts regardless of being protonic or non-protonic.

The gel may be used as a catalyst with no modification made to the carboxylic acid polymer or with a metal ion being chelated.

Similarly to the previous cases, the gel can be used as a catalyst in Knoevenagel condensation reaction with no modification made to the corresponding carboxylic acid polymer, and can be suitably used especially as a catalyst in a synthesis reaction of, for example, hydroxyalkanal with metal. The metal used herein is not limited in any particular manner. Examples of such a metal include copper, lead, nickel, zinc, iron, cobalt, chromium, manganese, bismuth, tin, antimony, and alkaline earth metals. The carboxylic acid polymer holding a metal allows the resultant gel to be suitably used especially as a catalyst in selective synthesis of acrylic acid esters.

The amount of the metal to the carboxylic acid polymer holding that metal is not limited in any particular manner, being specified properly depending upon the kind of the carboxylic acid polymer and the kind of the synthesis reaction in which the catalyst is used.

For example, when the gel is used as a catalyst in a synthesis reaction of hydroxyalkanal, the amount of the metal held by the carboxylic acid polymer is preferably in a range from 0.001 weight % to 10 weight , more preferably in a range from 0.001 weight % to 5 weight %, and even more preferably in a range from 0.01 weight % to 1 weight %. If the amount of the metal held is less than 0.001 weight %, expected results may not obtained from letting the carboxylic acid polymer hold a metal. By contrast, if the amount of the metal held is more than 10 weight %, the yield of hydroxyalkanal may decline. The word, "hold", herein is not limited to chelating, but may include salt formation, absorption, clathrate formation, etc. The metal held may be either a metal or ions. The ions may be an oxide, halogenide, sulfide, etc.

The method of letting the carboxylic acid polymers hold a metal is not limited in any particular manner. A conventional method, e.g. the aforementioned method, may be employed.

Alternatively, the gels, since prepared by swelling the corresponding carboxylic acid polymers in a dispersion medium, are more widely applicable than are the carboxylic acid polymers per se. For example, the three-dimensional reticular structure of the gels imparts molecule-sieving effects thereto, and allows the gels to be suitably used, for example, for refinement of sugar and as absorbing agents and filtering agents for separating a mixture of gasses and liquids.

The gels are highly responsive to heat and reversible in thermal expansion. Therefore a change in volume of the gels at high temperatures can be converted to pressure and thereby applied, as an example, for an actuator. The gels are also highly responsive to pH, being capable of altering their form (crosslinking density) according to acidity or alkalinity. Therefore, the gels can be suitably used for, as an example, a so-called drug delivery system according to which the gels containing a desired compound such as pharmaceuticals release the same in a particular pH environment such as in a human body. As explained so far, the gels exhibits a superior metal-ion-scavenging ability (chelating ability) and an extremely high acid strength in a non-protonic solvent, and in addition are responsive to pH and heat, being suitably applicable for a variety of purposes.

As described above, the carboxylic acid polymers and the gels thereof are also superior in metal-ion-scavenging ability (chelating ability), and can be suitably used as chelating agents, as an example. When the carboxylic acid polymers and the gels thereof are used as chelating agents, those chelating agents may contain a conventional, well-known chelating agent and other additives, in addition to the carboxylic acid polymers.

For a fuller understanding of the nature of the invention, reference should be made to the ensuing detailed description taken in conjunction with the accompanying drawing.

BEST MODES OF CARRYING OUT THE INVENTION

The following description will further discuss the present invention by means of embodiments, which are given for the purpose of illustration only, are not in any way intended to limit the scope of the present invention.

[FIRST EMBODIMENT]

A three-necked flask fitted with a thermometer, a stirrer, a dropping device, and a circulation cooling device was charged with 50 g of 2-diallylaminoethanethiol, and the content was stirred while being cooled with water. Meanwhile, the dropping device was charged with acrylic acid of the same amount in moles as the 2-diallylaminoethanethiol. Thereafter, the acrylic acid in the dropping device was added dropwise over a period of 10 hours, and the contents were then stirred for 5 hours to complete the reaction.

The reaction product thus obtained was analyzed to identify substances by element analysis, mass analysis, and $^1$H-NMR measurement. According to the element analysis, the molecular composition of the reaction product was 11.0 weight % carbon atoms, 19.2 weight % hydrogen atoms, 1.0 weight % nitrogen atoms, 2.1 weight oxygen atoms %, and 1.0 weight % sulfur atoms. The respective signals, i.e. ① δ 2.6 ppm–3.5 ppm (8H), ② δ 5.3 ppm–5.5 ppm (4H), ③ δ 5.7 ppm–5.9 ppm (4H), ④ δ 5.9 ppm–6.1 ppm (4H), and ⑤ δ 10.4 ppm–10.6 ppm (1H), of $^1$H-NMR using CDC$_3$1 as the solvent indicated the following structures:

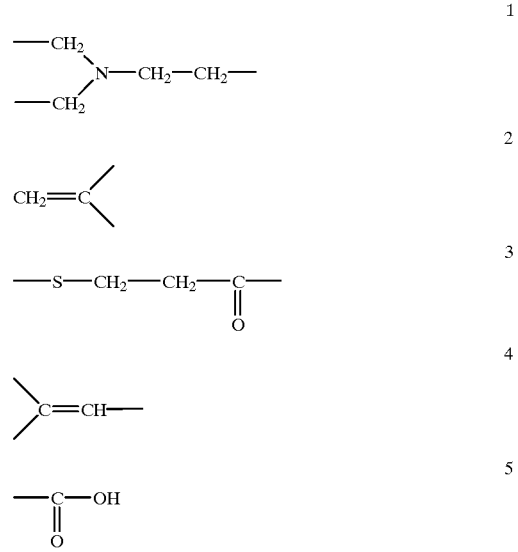

These data supported the structure represented by formula (9). So did the fragment ion peaks of (m/z)$^+$ 230 (M+1)$^+$, (m/z)$^+$ 10, 133, and 156 of MS. As a result, it was confirmed that the obtained reaction product was a new carboxylic acid monomer in accordance with the present invention, i.e. 6-(N,N-dipropenylamino)-4-thiahexane acid. The above reaction is shown below:

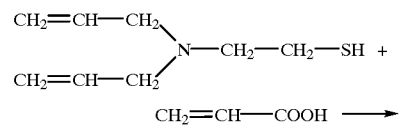

-continued

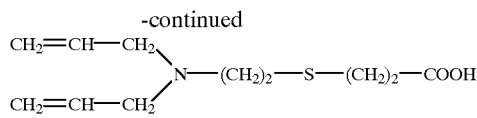

[SECOND EMBODIMENT]

A three-necked flask like the one used in the first embodiment was charged with 10 g of 2-allylaminoethanethiol, and the content was stirred while being cooled with water. Meanwhile, the dropping device was charged with acrylic acid of the same amount in moles as the 2-allylaminoethanethiol. Thereafter, the acrylic acid in the dropping device was added dropwise over a period of 2 hours, and the contents were then stirred for 5 hours to complete the reaction. The reaction product thus obtained was analyzed to identify substances by the same methods as in the first embodiment. As a result, it was confirmed that the obtained reaction product was a new carboxylic acid monomer in accordance with the present invention. The above reaction is shown below:

$$CH_2=CH-CH_2-NH-CH_2-CH_2-SH +$$
$$CH_2=CH-COOH \longrightarrow$$
$$CH_2=CH-CH_2-NH-(CH_2)_2-S-(CH_2)_2-COOH$$

[THIRD EMBODIMENT]

A three-necked flask like the one used in the first embodiment was charged with 5 g of 2-(allyl-(2-mercapto ethyl) aminoethanethiol, and the content was stirred while being cooled with water. Meanwhile, the dropping device was charged with acrylic acid of double the amount in moles of the 2-(allyl-(2-mercapto ethyl) aminoethanethiol. Thereafter, the acrylic acid in the dropping device was added dropwise over a period of 1 hour, and the contents were stirred for 5 hours to complete the reaction. Element analysis of the reaction product thus obtained confirmed that the reaction product contained 13.0 weight % carbon atoms, 23.2 weight % hydrogen atoms, 1.0 weight % nitrogen atoms, 3.8 weight oxygen atoms %, and 2.2 weight % sulfur atoms. Besides, the reaction product was analyzed to identify substances by the predetermined methods. As a result, it was confirmed that the obtained reaction product was a new carboxylic acid monomer in accordance with the present invention. The above reaction is shown below:

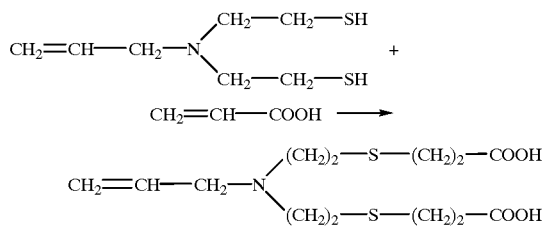

[FOURTH EMBODIMENT]

A reaction container fitted with a thermometer, a stirrer, a dropping device, and a circulation cooling device was charged with 400 g of cyclohexane as a solvent and 3 g of a predetermined suspension agent, and the contents were stirred. The reaction container was further charged with 30 g of a monomer component constituted by 6-(N,N-dipropenylamino)-4-thiahexane acid and acrylic acid, 0.96 g of trimethylolpropane triacrylate as a crosslinking agent, and 30 g of water as a solvent, and the contents were heated to the temperature of 70° C. Note that the 6-(N,N-dipropenylamino)-4-thiahexane acid was added so that the amount used of the 6-(N,N-dipropenylamino)-4-thiahexane acid in the monomer component equaled 30 mole %. Meanwhile, the dropping device was charged with 10 cc of a 0.5-weight-% water solution of 2,2'-azobis-(2-amidinopropane) dihydrochloride (product name V-50: available from Wako Pure Chemical Industries, Ltd.) as a polymerization initiator. Subsequently, the polymerization initiator in the dropping device was added dropwise to the reaction liquid over a period of about 20 minutes, and then the reaction liquid was stirred for 3 hours before stopping stirring. Subsequently, the reaction liquid was stored at room temperature overnight so as to mature reaction, then filtered, and dried at the temperature of 80° C. under decreased pressure. Consequently, 23 g of polymer was obtained. Analysis of the obtained polymer by the predetermined methods to identify substances, in addition to element analysis, confirmed that the polymer was a new carboxylic acid polymer containing about 30-mole-% 6-(N,N-dipropenylamino)-4-thiahexane acid. Element analysis confirmed that the polymer contained 54.1 weight % carbon atoms, 7.4 weight % hydrogen atoms, 4.0 weight % nitrogen atoms, 24.5 weight oxygen atoms %, and 9.9 weight % sulfur atoms. This, if calibrated into moles, showed that 27 mole % of the carboxylic groups contained in the resin are —NH—$(CH_2)_2$—S— $(CH_2)_2$—COOH groups.

[FIFTH EMBODIMENT]

A reaction container fitted with a thermometer, a stirrer, and a circulation cooling device was charged with 70.2 g of a monomer component constituted by 6-(N,N-dipropenylamino)-4-thiahexane acid and acrylic acid, 400 g of toluene as a solvent, and 1.7 g of divinylbenzene as a crosslinking agent, and the contents were stirred. Note that the 6-(N,N-dipropenylamino)-4-thiahexane acid was added so that the amount used of the 6-(N,N-dipropenylamino)-4-thiahexane acid in the monomer component equaled 30 mole %. After heating the reaction liquid to the temperature of 80° C., 0.1 g of 2,2'-azobis-(2,4-dimethylvaleronitrile) (product name V-65: available from Wako Pure Chemical Industries, Ltd.) was added as a polymerization initiator, and the reaction liquid was reacted for 5 hours to complete the reaction. Subsequently, the obtained reaction product was filtered, and then dried at the temperature of 80° C. under decreased pressure. Consequently, 28 g of polymer was obtained. An analysis of the obtained polymer by the same methods as in the fourth embodiment confirmed that the polymer was a new carboxylic acid polymer containing about 30-mole-% 6-(N,N-dipropenylamino)-4-thiahexane acid.

[SIXTH EMBODIMENT]

A reaction container fitted with a thermometer, a stirrer, a dropping device, and a circulation cooling device was charged with 8 kg of cyclohexane as a solvent and 60 g of a predetermined suspension agent, and the contents were stirred. Subsequently, the reaction container was charged with 597 g of a monomer component constituted by 6-(N, N-dipropenylamino)-4-thiahexane acid and acrylic acid, 56 g of trimethylolpropane triacrylate as a crosslinking agent, and 751 g of water as a solvent, and the contents were heated to the temperature of 70° C. Note that the 6-(N,N-dipropenylamino)-4-thiahexane acid was added so that the amount used of the 6-(N,N-dipropenylamino)-4-thiahexane acid in the monomer component equaled 5 mole %. Meanwhile, the dropping device was charged with 200 cc of a 0.5-weight-% water solution of 2,2'-azobis-(2-amidinopropane) dihydrochloride (product name V-50: available from Wako Pure Chemical Industries, Ltd.) as a polymerization initiator. Subsequently, the polymerization initiator in the dropping device was added dropwise to the reaction liquid over a period of 20 minutes, and then the reaction liquid was further stirred for 3 hours before stopping stirring. Subsequently, the reaction liquid was stored at room temperature overnight so as to mature reaction. Consequently, a bead-like reaction product of 0.1 mm to 2 mm was obtained.

Thereafter the obtained bead-like reaction product was transferred to a rotary evaporator for cyclohexane being distilled away, and then dried at the temperature of 80° C. under decreased pressure. Consequently, 540 g of polymer was obtained. An analysis of the obtained polymer by the same methods as in the fourth embodiment confirmed that the polymer was a new carboxylic acid polymer in accordance with the present invention. Thereafter, the carboxylic acid polymer was immersed in ion-exchange water for 48 hours at room temperature. Consequently, a gel containing 4 g to 6 g of water per 1 g of the carboxylic acid polymer was obtained.

[SEVENTH EMBODIMENT]

0.6 g of the carboxylic acid polymer obtained in the sixth embodiment was immersed in a water solution of copper acetate of 1 M which was maintained at room temperature, and then sufficiently washed in ion-exchange water. Consequently, a blue gel was obtained. Subsequently, the gel was washed in 50 g of a water solution of hydrochloric acid of 0.9 M. An analysis of the washing liquid by ICP (Inductively Coupled Plasma) spectrometry confirmed that 0.41-g copper ions were chelated. This corresponds to 6.4 mmol of copper ions being chelated by 1 cc of polymer.

[EIGHTH EMBODIMENT]

A blue gel was obtained by the same operation as in the seventh embodiment, except that a water solution of copper sulfate of 1 M was used in lieu of the water solution of copper acetate of 1 M. Subsequently, the gel was washed and analyzed by the same methods as in the seventh embodiment. The analysis confirmed that 0.40-g copper ions were chelated. This corresponds to 6.1 mmol of copper ions being chelated by 1 cc of the carboxylic acid polymer obtained in the first embodiment.

[NINTH EMBODIMENT]

A blue gel was obtained by the same operation as in the seventh embodiment, except that a water solution of copper sulfate of 0.2 M was used in lieu of the water solution of copper acetate of 1 M. Subsequently, the obtained gel was immersed in a water solution of hydrochloric acid of pH=1 for not less than 10 days. This operation was conducted using a water solution of hydrochloric acid of various pH values ranging from 1 to 7. The gel immersed in a water solution of hydrochloric acid of pH≧3 maintained the blue color thereof.

[TENTH EMBODIMENT]

The gel obtained in the sixth embodiment was measured for reversible thermal expansion rate to evaluate the heat response thereof. After measurement of the volume of the gel obtained in the sixth embodiment, the gel was immersed in ion-exchange water and heated at the temperature of 90° C. for a predetermined period of time. Consequently, the gel exhibited a volume expansion 1.9 times that at room temperature. This shows that the swelling ratio of the gel at the temperature of 90° C. equals 1.9 times that at room temperature. The gel, when cooled down back to room temperature, restored the original volume thereof.

[ELEVENTH EMBODIMENT]

The gel obtained in the sixth embodiment was used as a catalyst in a hydration reaction of acrolein. A reaction container fitted with a thermometer and a stirrer was first charged with 20 g of water and thereafter charged with a predetermined amount of acrolein so that the concentration in the water solution equaled 28%. Next, the gel obtained from the above reaction was added into the water solution as a catalyst so that the amount used of the carboxylic acid polymer equaled 8 g. Thereafter, the acrolein was hydrated by reacting the reaction solution at the temperature of 90° C. for 5 hours with continuous stirring.

After completion of the reaction, the reaction solution was filtered. It was found as a result of an analysis of the filtrate by predetermined methods that the conversion of the acrolein was 72% and that the total selectivity of the hydration reaction product, i.e. 3-hydroxypropanal, and a dimer thereof was 90%. The conversion of the acrolein and the selectivity of 3-hydroxypropanal and the dimer thereof were defined as follows:

Conversion of Acrolein (%)=(Acrolein Consumed in Moles/Acrolein Supplied in Moles)×100

Selectivity of 3-Hydroxypropanal (%)=(Acrolein Converted into 3-Hydroxypropanal in Moles/Acrolein Consumed in Moles)×100

Selectivity of Dimer of 3-Hydroxypropanal (%)=(Acrolein Converted into Dimer of 3-Hydroxypropanal in Moles/Acrolein Consumed in Moles)×100

The amounts of the acrolein, 3-hydroxypropanal, and the dimer of 3-hydroxypropanal can be determined by a conventional method such as gas chromatography.

The results of the first to ninth embodiments show that the present invention could produce a gel that scavenged (chelated) a large amount of metal ions per unitary volume thereof and that was superior in chelating ability even under low pH conditions. The results of the tenth and eleventh embodiments show that the gel possessed reversible thermal expansion, could be suitably used as a catalyst in a hydration reaction of acrolein, and yielded 3-hydroxypropanal and the dimer thereof at high selectivities.

[TWELFTH EMBODIMENT]

A reaction container fitted with a thermometer, a stirrer, a dropping device, and a circulation cooling device was charged with 8 kg of cyclohexane as a solvent and a predetermined suspension agent, and the contents were stirred. Subsequently, the reaction container was charged with 580 g of a monomer component constituted by N,N-diallylamine and acrylic acid, 28 g of trimethylolpropane triacrylate as a crosslinking agent, and 2400 g of water as a solvent, and the contents were heated to the temperature of 70° C. Note that the N,N-diallylamine was added so that the amount used of the N,N-diallylamine in the monomer component equaled 5 mole %. Meanwhile, the dropping device was charged with a predetermined amount of a water solution of 2,2'-azobis-(2-amidinopropane) dihydrochloride (product name V-50: available from Wako Pure Chemical Industries, Ltd.) of a predetermined concentration as a polymerization initiator. Subsequently, the polymerization initiator in the dropping device was added dropwise to the reaction liquid over a period of 20 minutes, and then the reaction liquid was further stirred for 3 hours before stopping stirring. Subsequently, the reaction liquid was stored at a predetermined temperature overnight so as to mature reaction. Consequently, a bead-like reaction product of 0.1 mm to 2 mm was obtained.

Thereafter the obtained bead-like reaction product was transferred to a rotary evaporator to scavenge (chelated) the cyclohexane, and then dried at the temperature of 80° C. under decreased pressure for a predetermined period of time. Consequently, 600 g of polymer, i.e. a carboxylic acid polymer in accordance with the present invention, was obtained. The carboxylic acid polymer obtained was swollen by immersing the carboxylic acid polymer in ion-exchange water for a predetermined period of time at room temperature. Consequently, a gel containing 4 g to 6 g of water per 1 g of the carboxylic acid polymer was obtained.

[THIRTEENTH EMBODIMENT]

The carboxylic acid polymer obtained in the twelfth embodiment was immersed for 70 hours in a water solution of copper sulfate of 0.2 M which was maintained at a predetermined temperature, and then sufficiently washed in a predetermined amount of ion-exchange water. Consequently, a blue gel was obtained. Subsequently, the obtained gel was immersed in a water solution of hydrochloric acid of pH=1 for not less than 10 days. This operation was conducted using a water solution of hydrochloric acid of various pH values ranging from 1 to 7. The gel immersed in a water solution of hydrochloric acid of pH≧4 maintained the blue color thereof.

[FOURTEENTH EMBODIMENT]

The gel obtained in the twelfth embodiment was measured for acid strength in a protonic solvent by titration of indicator. To be more specific, the gel swollen in water was stirred in water, and then an indicator was titrated according to indicator titration method to measure the surface acid strength. The results were pK=+2.0 to +3.3. This corresponds to 0.0003 weight %a to 0.005 weight % of sulfate water solution.

[FIFTEENTH EMBODIMENT]

The gel obtained in the twelfth embodiment was measured for acid strength in a non-protonic solvent by titration of indicator. To be more specific, the gel swollen in water was stirred in dioxane, and then an indicator was titrated according to indicator titration method to measure the surface acid strength. The results were pK=+0.8 to +1.7. This corresponds to 0.02 weight % to 1.7 weight % of sulfate water solution.

[SIXTEENTH EMBODIMENT]

The gel obtained in the twelfth embodiment was measured for reversible thermal expansion rate. After measurement of the volume of the gel obtained in the first embodiment, the gel was immersed in ion-exchange water and heated at the temperature of 90° C. for a predetermined period of time. Consequently, the gel exhibited a volume expansion 1.48 times that at room temperature. This shows that the swelling ratio of the gel at the temperature of 90° C. equals 1.48 times that at room temperature. The gel, when cooled down back to room temperature, restored the original volume thereof.

[SEVENTEENTH EMBODIMENT]

The gel obtained in the twelfth embodiment was used as a catalyst in a hydration reaction of acrolein. A reaction container fitted with a thermometer and a stirrer was first charged with a predetermined amount of water and thereafter charged with a predetermined amount of acrolein so that the concentration in the water solution equaled 28%. Next, a predetermined amount of the gel was added into the water solution as a catalyst. Thereafter, the acrolein was hydrated by reacting the reaction solution at 90° C. for 5 hours with continuous stirring.

After completion of the reaction, the reaction solution was filtered. It was found as a result of an analysis of the filtrate by predetermined methods that the conversion of the acrolein was 57% and that the total selectivity of the hydration reaction product, i.e. 3-hydroxypropanal, and a dimer thereof was 89%. The conversion of the acrolein and the selectivities of 3-hydroxypropanal and the dimer thereof were defined as shown in the eleventh embodiment. The results of the twelfth to seventeenth embodiments show that the present invention could produce a gel that scavenged (chelated) a large amount of metal ions per unitary volume thereof and that was superior in chelating ability even under low pH conditions, and also show that the gel possessed reversible thermal expansion, could be suitably used, for example, as a catalyst in a hydration reaction of acrolein, and yielded 3-hydroxypropanal and the dimer thereof at high selectivities.

INDUSTRIAL APPLICABILITY

A carboxylic acid polymer in accordance with the present invention is superior in metal-ion-scavenging ability (chelating ability), and can be suitably used, for example, for recovery of metals and disposal of metal-containing waste liquids. Therefore, the carboxylic acid polymer can be suitably used as a chelating agent.

The carboxylic acid polymer, when containing a nitrogen atom, a sulfur atom, and a carboxylic group in one molecule, can stabilize metal ions in form that would not generally exist. By using the carboxylic acid polymer as a gel, the carboxylic acid polymer is more widely applicable, for example, to molecule-sieving, refinement of sugar, and drug delivery system.

What is claimed is:

1. A carboxylic acid polymer having as the main chain thereof a group of a structure represented by General Formula (1):

$$X-(CH_2)_{n4}-S-(CH_2)_{m4}-COOH \qquad (1)$$

where X is the principal segment of the carboxylic acid polymer, n4 is an integer from 0 to 6, and m4 is an integer from 0 to 6.

2. A carboxylic acid polymer formed by polymerizing a monomer component containing a carboxylic acid monomer, the carboxylic acid monomer containing an allylamino group and a carboxylic group and having at least one kind of bond selected from the group consisting of an amino bond, an ether bond, and thioether bond.

3. The carboxylic acid polymer as set forth in claim 2, wherein the carboxylic acid polymer is formed by polymerizing a monomer component containing a carboxylic acid monomer represented by General Formula (3):

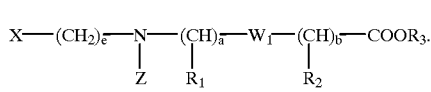

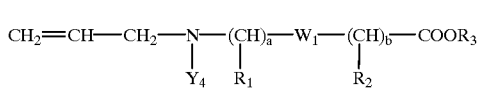

where $Y_4$ is a hydrogen atom, an allyl group, or a $—(CHR_4)_c—W_2—(CHR_5)_d—COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an —NH— group, an —S— group, or an —O— group, and each of a, b, c, and d, independent of the others, is an integer from 0 to 6.

4. The carboxylic acid polymer as set forth in claim 3, wherein the carboxylic acid monomer is of a structure represented by formula (9):

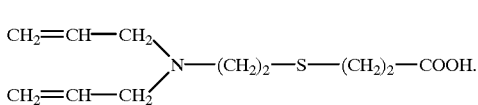

5. The carboxylic acid polymer as set forth in claim 3, wherein the carboxylic acid monomer is of a structure represented by formula (10):

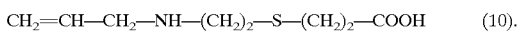

6. The carboxylic acid monomer as set forth in claim 3, wherein the carboxylic acid monomer is of a structure represented by formula (11):

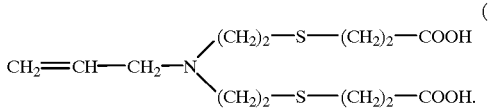

7. A carboxylic acid polymer containing a functional group of a structure represented by General Formula (2):

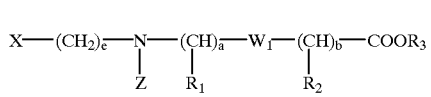

where Z is a hydrogen atom, a $—(CHR_4)_c—W_2—(CHR_5)_d—COOR_6$ group, of a $—(CH_2)_f—X$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$ independent of the other, is either an —NH— group, an —S— group, or an —O— group, X is the principal segment of the carboxylic acid polymer, and each of a, b, c, d, e, and f, independent of the others, is an integer from 0 to 6.

8. A method of manufacturing a carboxylic acid polymer, comprising the step of polymerizing a monomer component containing a carboxylic acid monomer represented by General Formula (3):

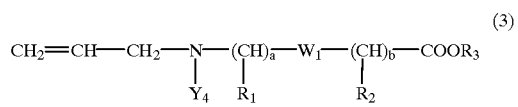

where $Y_4$ is a hydrogen atom, an allyl group, or a $—(CHR_4)_c—W_2—(CHR_5)_d—COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an —NH— group, an —S— group, or an —O— group, and each of a, b, c, and d, independent of the others, is an integer from 0 to 6.

9. A carboxylic acid monomer, containing an allylamino group and a carboxylic group and having at least one kind of bond selected from the group consisting of an amino bond, an ether bond, and a thioether bond.

10. The carboxylic acid monomer as set forth in claim 9, wherein the carboxylic acid monomer is of a structure represented by General Formula (3):

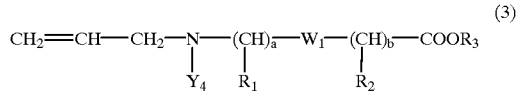

where $Y_4$ is a hydrogen atom, an allyl group, or a $—(CHR_4)_c—W_2—(CHR_5)_d—COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an —NH— group, an —S— group, or an —O— group, and each of a, b, c, and d, independent of the others, is an integer from 0 to 6.

11. The carboxylic acid monomer as set forth in claim 10, wherein the carboxylic acid monomer is of a structure represented by formula (9):

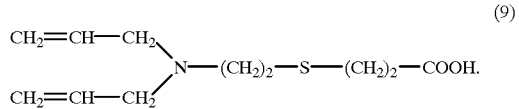

12. The carboxylic acid monomer as set forth in claim 10, wherein the carboxylic acid monomer is of a structure represented by formula (10):

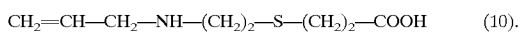

13. The carboxylic acid monomer as set forth in claim 10, wherein the carboxylic acid monomer is of a structure represented by formula (11):

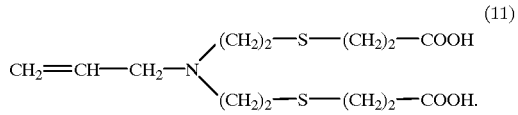

(11)

14. A method of manufacturing a carboxylic acid monomer, comprising the step of reacting (meth)acylic acid with a compound represented by General Formula (12):

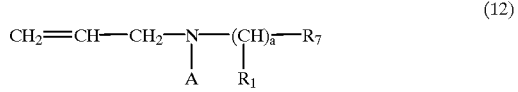

(12)

where A is a hydrogen atom, an allyl group, or a —$(CHR_4)_c$—$R_8$ group, each of $R_1$ and $R_4$, independent of the other, is either a hydrogen atom or an alkyl group of a carbon number from 1 to 6, each of $R_7$ and $R_8$, independent of the other, is either an —SH group, an —OH group, or an —$NH_2$ group, and each of a and c, independent of the other, is an integer from 0 to 6.

15. A gel, formed by swelling, in a dispersion medium, a carboxylic acid polymer formed by polymerizing a monomer component containing a carboxylic acid monomer represented by General Formula (3):

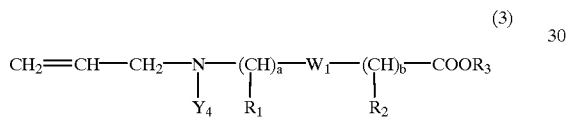

(3)

where $Y_4$ is a hydrogen atom, an allyl group, or a —$(CHR_4)_c$—$W_2$—$(CHR_5)_d$—$COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an —NH— group, an —S— group, or an —O— group, and each of a, b, c, and d, independent of the others, is an integer from 0 to 6.

16. The gel as set forth in claim 15, wherein the carboxylic acid monomer is of a structure represented by formula (9):

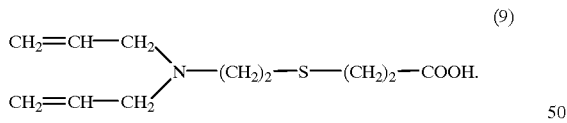

(9)

17. The gel as set forth in claim 15, wherein the carboxylic acid monomer is of a structure represented by formula (10):

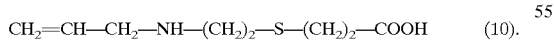

$CH_2$=CH—$CH_2$—NH—$(CH_2)_2$—S—$(CH_2)_2$—COOH    (10).

18. The gel as set forth in claim 15, wherein the carboxylic acid monomer is of a structure represented by formula (11):

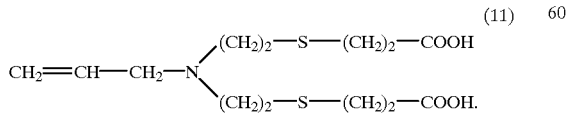

(11)

19. A gel, formed by swelling, in a dispersion medium, a carboxylic acid polymer formed by copolymerizing an unsaturated monomer (A) containing a carboxylic group and a nitrogen-containing unsaturated compound selected from the group consisting of vinylpyridines, N-vinyl carbazoles, allylamines, 4-(N,N-dialkylamino) alkylstyrenes, 6-(N-propenylamino)-4-thiahexane acid, and 6-(N,N-dipropenylamino)-4-thiahexane acid.

20. The gel as set forth in claim 19, wherein said nitrogen-containing unsaturated compound is an allylamine.

21. A gel, formed by swelling, in a dispersion medium, a carboxylic acid polymer having at least one structure selected from the group consisting of structures represented by General Formulas (4), (5), (7) or (8):

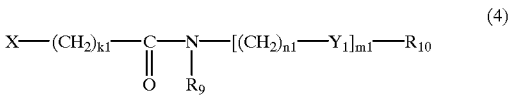

(4)

where each of $R_9$ and $R_{10}$, independent of the other, is either a hydrogen atom, a hydrocarbonate group of a carbon number from 1 to 5, or a —$(C_2)_{p1}$—X group, p1 is an integer from 0 to 6, k1 is an integer from 0 to 6, m1 is an integer from 0 to 6, n1 is an integer from 0 to 6, Y1 is an —O— group, an —S— group, or an —$NR_{11}$— group, $R_{11}$ is a hydrogen atom or a hydrocarbon of a carbon number from 1 to 5, and X is the principal segment of the carboxylic acid polymer;

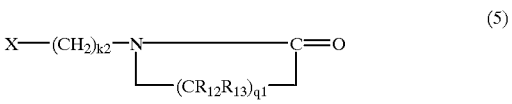

(5)

where each of $R_{12}$ and $R_{13}$, independent of the other, is either a hydrogen atom or a hydrocarbonate group of a carbon number from 1 to 5, k2 is an integer from 0 to 6, and q1 is an integer from 3 to 6;

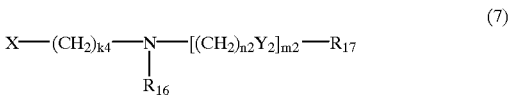

(7)

where $R_{16}$ hydrogen atom, a hydrocarbonate group of a carbon number from 1 to 5, or a —$(CH_2)_{p4}$—X group, p4 is an integer from 0 to 6, k4 is an integer from 0 to 6, n2 is an integer from 0 to 6, Y2 is an —O— group, an —S— group, an —$NR_{18}$— group, or a —$CH_2$— group, $R_{18}$ is a hydrogen atom or a hydrocarbonate group of a carbon number from 1 to 5, X is the principal segment of the carboxylic acid polymer, m2 is an integer from 0 to 6, $R_{17}$ is a hydrogen atom, a hydrocarbonate group of a carbon number from 1 to 5, a —$(CH_2)_{p5}$X group, or a Brønsted acid residual group when $m_2 \neq 0$, and is a hydrogen atom, a hydrocarbonate group of a carbon number from 1 to 5, or a —$(CH_2)_{p5}$X group when $m_2 \neq 0$, and p5 is an integer from 0 to 6; and

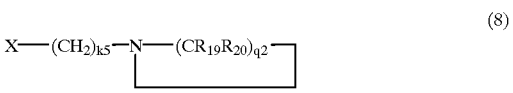

(8)

where each of $R_{19}$ and $R_{20}$, independent of the other, is either a hydrogen atom or a hydrocarbonate group of a carbon number from 1 to 5, k5 is an integer from 0 to 6, q2 is an integer from 4 to 7, and X is the principal segment of the carboxylic acid polymer.

22. A chelating agent, comprising a carboxylic acid polymer formed by polymerizing a monomer component containing a carboxylic acid monomer represented by General Formula (3):

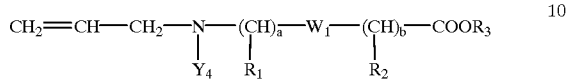
(3)

where $Y_4$ is a hydrogen atom, an allyl group, or a —$(CHR_4)_c$—$W_2$—$(CHR_5)_d$—$COOR_6$ group, each of $R_1$, $R_2$, $R_3$, $R_4$, $R_5$, and $R_6$, independent of the others, is either a hydrogen atom or an alkyl group of a carbon number from 1 to 6, each of $W_1$ and $W_2$, independent of the other, is either an —NH— group, an —S— group, or an —O— group, and each of a, b, c, and d, independent of the others, is an integer from 0 to 6.

23. The chelating agent as set forth in claim 22, wherein the carboxylic acid monomer is of a structure represented by formula (9):

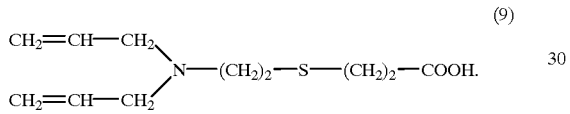
(9)

24. The chelating agent as set forth in claim 22, wherein the carboxylic acid monomer is of a structure represented by formula (10):

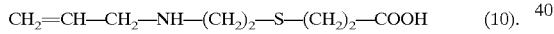
(10).

25. The chelating agent as set forth in claim 22, wherein the carboxylic acid monomer is of a structure represented by formula (11):

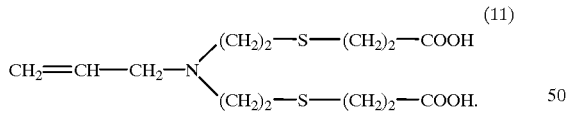
(11)

26. A chelating agent comprising a carboxylic acid polymer having at least one structure selected from the group consisting of structures represented by General Formulas (4), (5), (7) or (8):

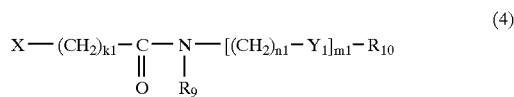
(4)

where each of $R_9$ and $R_{10}$, independent of the other, is either a hydrogen atom, a hydrocarbonate group of a carbon number from 1 to 5, or a —$(CH_2)_{p1}$—X group, p1 is an integer from 0 to 6, k1 is an integer from 0 to 6, m1 is an integer from 0 to 6, n1 is an integer from 0 to 6, Y1 is an —O— group, an —S— group, or an —$NR_{11}$— group, $R_{11}$ is a hydrogen atom or a hydrocarbon of a carbon number from 1 to 5, and X is the principal segment of the carboxylic acid polymer;

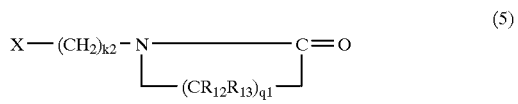
(5)

where each of $R_{12}$ and $R_{13}$, independent of the other, is either a hydrogen atom or a hydrocarbonate group of a carbon number from 1 to 5, k2 is an integer from 0 to 6, and q1 is an integer from 3 to 6;

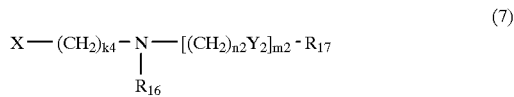
(7)

where $R_{16}$ is a hydrogen atom, a hydrocarbonate group of a carbon number from 1 to 5, or a —$(CH_2)_{p4}$—X group, p4 is an integer from 0 to 6, k4 is an integer from 0 to 6, n2 is an integer from 0 to 6, Y2 is an —O— group, an —S— group, an —$NR_{18}$— group, or a —$CH_2$— group, $R_{18}$ is a hydrogen atom or a hydrocarbonate group of a carbon number from 1 to 5, X is the principal segment of the carboxylic acid polymer, m2 is an integer from 0 to 6, $R_{17}$ is a hydrogen atom, a hydrocarbonate group of a carbon number from 1 to 5, a —$(CH_2)_{p5}$—X group, or a Brønsted acid residual group when $m_2 \neq 0$, and is a hydrogen atom, a hydrocarbonate group of a carbon number from 1 to 5, or a —$(CH_2)_{p5}$—X group when $m_2=0$, and p5 is an integer from 0 to 6; and

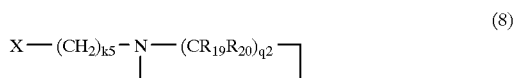
(8)

where each of $R_{19}$ and $R_{20}$, independent of the other, is either a hydrogen atom or a hydrocarbonate group of a carbon number from 1 to 5, k5 is an integer from 0 to 6, q2 is an integer from 4 to 7, and X is the principal segment of the carboxylic acid polymer.

* * * * *